United States Patent [19]

Cusack et al.

[11] Patent Number: 4,730,160

[45] Date of Patent: Mar. 8, 1988

[54] PROGRAMMABLE THERMAL EMULATOR TEST DIE

[75] Inventors: Michael D. Cusack, Monument; Christopher A. Freymuth, Colorado Springs, both of Colo.

[73] Assignee: United Technologies Corporation, Hartford, Conn.

[21] Appl. No.: 841,975

[22] Filed: Mar. 20, 1986

[51] Int. Cl.$^4$ ............................................. G01N 25/18
[52] U.S. Cl. ................................ 324/158 R; 219/209; 357/28; 374/44; 374/152
[58] Field of Search ..................... 324/158 R; 374/152, 374/43, 44, 57; 357/28; 219/209, 210, 543

[56] References Cited

U.S. PATENT DOCUMENTS 3,781,515  12/1973  Morris, Jr. et al. ............... 357/28 X

FOREIGN PATENT DOCUMENTS 399086  2/1974  U.S.S.R. ............................... 219/209

OTHER PUBLICATIONS

IBM Technical Disclosure Bulletin, Reilly et al., "Self Contained Chip Heater", vol. 14, No. 6, Nov. 1971, p. 1770.

IBM Technical Disclosure Bulletin, Yu, "Self-Heating Test Chip for Reliability Life Test", vol. 25, No. 7B, Dec. 1982, p. 3651.

Primary Examiner—Reinhard J. Eisenzopf
Assistant Examiner—Stephen M. Baker
Attorney, Agent, or Firm—J. Kevin Grogan

[57] ABSTRACT

A novel test die for emulating the thermal characteristics of functional product dies includes a plurality of concentric emulator ring configurations fabricated about the die center, each having a plurality of heating resistors approximately forming a rectangle, a plurality of sense diodes located in proximity to the heating resistors and a plurality of hot spot resistors located in proximity to both the heating resistors and the sense diodes. Metallic interconnections are formed on the die which selectively provide each of the heating resistors and hot spot resistors with excitation signals and present signals from the sense diodes indicative of the voltage thereacross.

9 Claims, 4 Drawing Figures

PROGRAMMABLE THERMAL EMULATOR TEST DIE

DESCRIPTION

TECHNICAL FIELD

This invention relates to integrated circuit die test apparatus and in particular to a programmable thermal emulator die for simulating thermal characteristics of selectable size and power distributions.

BACKGROUND ART

Thermal characteristics of integrated circuits have become more important as current densities increase. Even low power silicon technology such as Complimentary Metal Oxide Semiconductor (CMOS) have high enough current densities to warrent circuit and package design that compensates for these increased thermal loads. It is well known in the art that high operating temperatures can deleteriously affect a lifetime of a circuit. For CMOS devices, junction temperatures under 125° C. are low enough to ensure long term operation. The onset of short term failure with CMOS circuits occurs above 125° C.

Individual high lead count packages are utilized for a whole spectrum of integrated circuit dies. Each die will have its own distinct thermal signature. Moreover, an integrated circuit will have several thermal signatures that are a function of the signals received by the device. To be useful for more than one application, a test die must possess the broadest range of power distribution emulation and die sizes. Given the wide variety of packaging materials, component assemblies and interconnect technologies, prior art test dies designed for specific applications have limited utility.

Increasing circuit densities magnify the effect of interconnect design on a device's thermal signature. High lead count packaging interconnect techniques include tape automated bonding (TAB) and flip chip technologies in addition to conventional wire bonding approaches. Prior art test dies do not address the effect of interconnect design on a thermal signature and only allow for wire bond interconnection of the die to the package.

DISCLOSURE OF INVENTION

An object of the present invention is to provide a programmable test die for selectively emulating the various thermal characteristics of a range of functional product dies.

According to the present invention, a programmable die for emulating the thermal characteristics of a functional product die includes a plurality of emulator ring configurations fabricated on a surface of the die about its center. Each emulator ring configuration includes a resistor group having a plurality of heating resistors approximately forming a rectangle about the center. Also included are a plurality of sense diodes formed in proximity to the heating resistors and a plurality of hot spot resistors formed in proximity to the heating resistors and the sense diodes. The programmable die also includes a metallic interconnection formed on the surface which selectively provides each of the heating resistors and hot spot resistors with electrical excitation signals and for providing signals indicative of the voltage across the sense diodes.

BEST MODE FOR CARRYING OUT THE INVENTION

Figure 1:
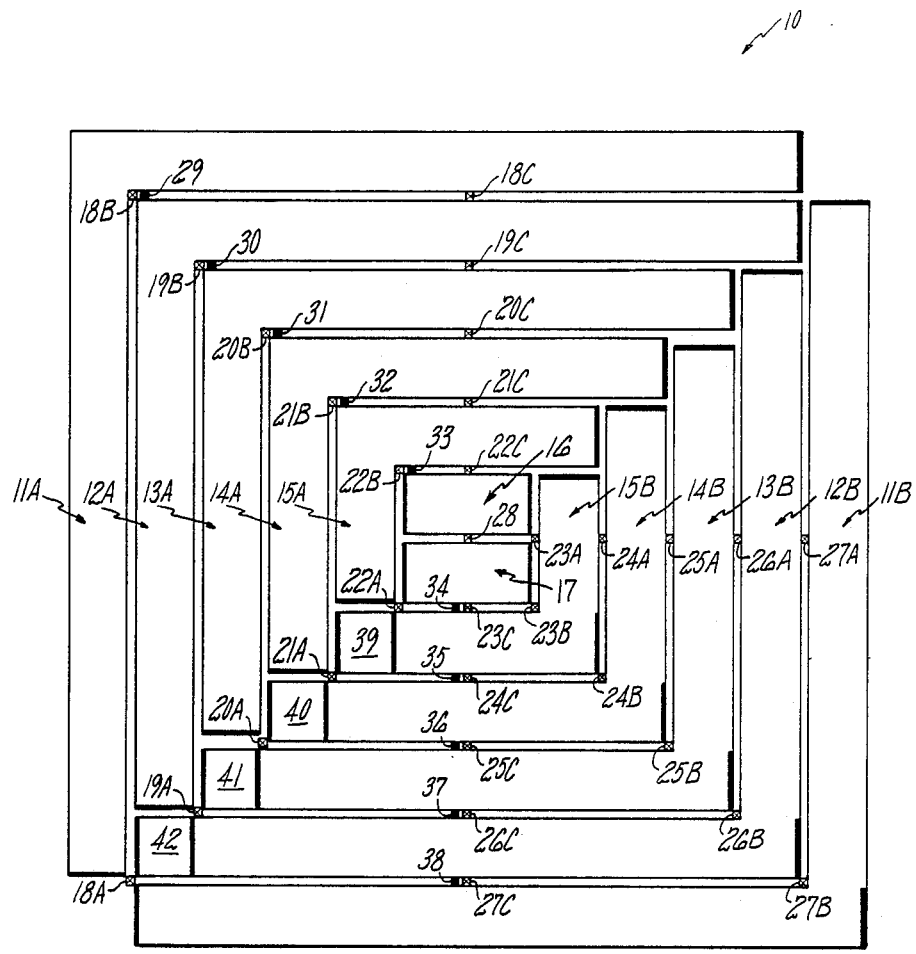
FIG. 1 is an illustration of a portion of a programmable thermal emulator test die provided according to the present invention.

Referring first to FIG. 1, in an illustration of a programmable thermal emulator test die provided according to the present invention, a programmable thermal emulator test die 10 includes concentric emulator ring configurations comprised of heating resistor groups 11A, 11B–15A, 15B, fabricated about center heating resistors 16, 17. Each of the resistor groups 11A–15A include triplet sense diodes 18A, 18B, 18C–22A, 22B, 22C and the resistor groups 11B–15B include triplet sense diodes 23A, 23B, 23C–27A, 27B, 27C. A sense diode 28 is positioned between center heating resistor 16, 17. The heating resistor groups 11A–15A further include hot spot resistors 29–33 and the resistor groups 11B–15B include hot spot resistors 34–38. Finally, segment resistors 39–42 may be included in each ring to fill in any gaps resulting from positioning of the individual groups. As detailed hereinafter with respect to FIG. 2, the relative positioning of the sense diodes to the hot spot resistors and the sense diodes to the heating resistors is selected to provide improved accuracy in heating and temperature sensing.

Test dies such as that provided according to the present invention are used to generate thermal profiles for evaluating the thermal characteristics of die package designs and die-attach materials and techniques. These dies are often used in conjunction with test systems, such as that disclosed in the commonly owned copending U.S. patent application Ser. No. 841,634 filed on even date herewith by James B. Stacey, et al, and entitled "A Programmable Test System For Integrated Circuit Dies".

The number of heating resistor groups is selected in dependence on the size of the die to be emulated. The simulated die size is determined by the area of the heating resistors for each concentric group, and is larger than the resistor area by approximately 15 mils per side, assuming thermal gradients of 45° C. and a die thickness of approximately 0.015 inches, as in the best mode embodiment. For example, an emulated square die size of approximately 60 mils (0.060 inches) corresponds to a simulated die size of 90 mils. In the best mode embodiment the width of each heating resistor is approximately 0.029 inches.

Each resistor group 11A, 11B–15A, 15B with the exception of the center ones 16, 17, is comprised of a plurality of heating resistors electrically connected in series by conventional metallized interconnections described hereinafter with respect to FIG. 4. The resistor groups may be separately addressed, and energized. Similarly, each resistor in a resistor group can be separately addressable. The arrangement enables complete heating of the die or selected areas thereof and more accurately resembles a functional product die.

Each heating resistor is fabricated using conventional CMOS techniques and materials. In the best mode embodiment each heating resistor is comprised of polysilicon of uniform width. Those skilled in the art will note that polysilicon resistance can be adjusted by altering the doping of the polysilicon resistor or the width or thickness thereof. The polysilicon is deposited by conventional techniques and patterned using standard photolithography. Diffused resistors can be substituted for those made from polysilicon but are less desirable. Their inherent low breakdown voltage limits the voltage range of the die. Heating resistors fabricated from polysilicon enable the die to dissipate power at a broad range of levels.

Figure 2:
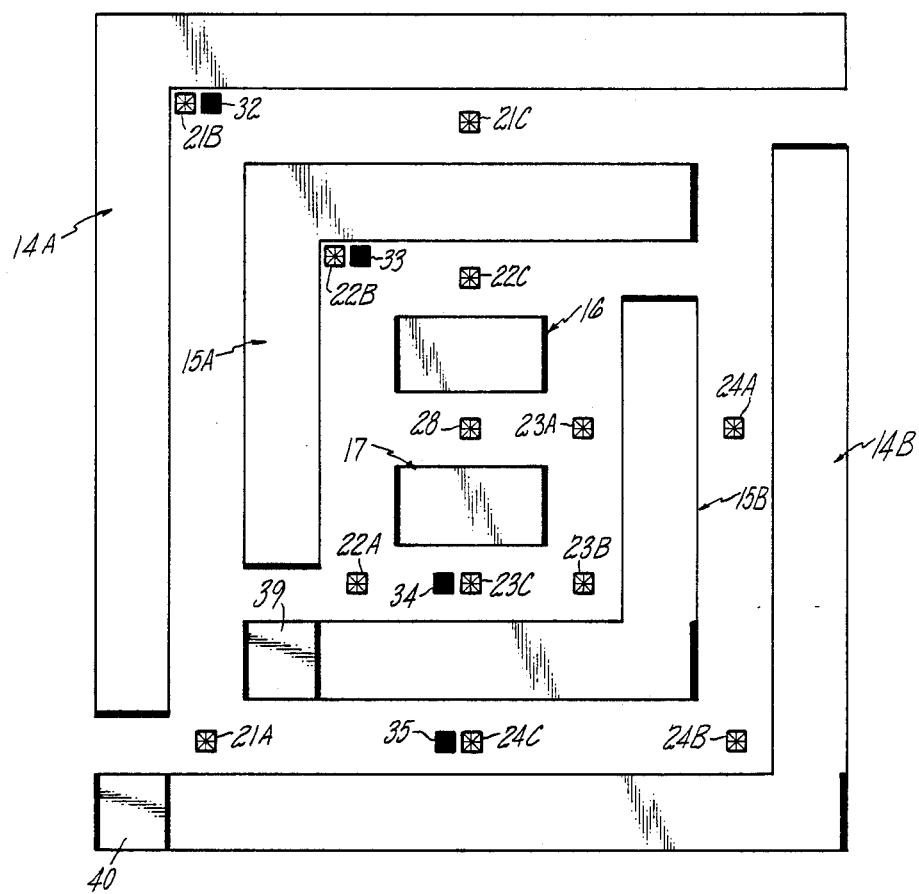
FIG. 2 is an illustration showing the position of selected circuit components used in the programmable thermal emulator test die of FIG. 1.

FIG. 2 is an illustration showing the positional relationship between hot spot resistors, sense diodes and heating resistor assemblies for the resistor group 14A, 14B, 15A, 15B, 16 and 17 of FIG. 1. It is well known in the art that in operation a functional product die displays a variety of thermal signatures. It is important that a functional product die's circuit layout design and package anticipate the full range of temperatures which will be reached by the die or portions thereof so that compensation can be introduced and life-shortening high temperatures avoided.

Product dies display a variety of thermal signatures generated in response to excitation signals. One set of excitation signals results in a broad power distribution throughout the die and produces thermal signatures characterized by distributed heating. One or more resistor groups in a test die provided according to the present invention are energized to provide thermal emulation of this kind of product die operation.

Other product dies have power intensive circuits or components thereof and will produce intense local heating in operation. To emulate these thermal signatures a plurality of hot spot resistors are located within each emulator ring configuration. These resistors provide substantial local heating, and in the best mode embodiment each comprises a polysilicon resistor whose structure and fabrication is similar to the heating resistors described hereinabove.

The highest local die temperature is generated by locating a hot spot resistor 32, in the included angle of the resistor group 14A, and energizing it in combination with the group resistor. Similarly, hot spot resistor 33 is located adjacent to resistor group 15A. Additional thermal profiles are produced when hot spot resistor 35 is energized alone or in combination with resistor group 14B. Other thermal profiles can be generated when some or all of the resistors of other emulator ring configurations are energized in conjunction therewith. The plurality of heating and hot spot resistors and their respective locations provide, to first order, emulation of highest to lowest die temperatures and greatest to smallest thermal gradients within the die with a minimum number of die elements.

Local temperature measurement is accomplished with signals received from sense diodes fabricated as part of an emulator ring configuration. As described hereinafter with respect to FIG. 2, the sense diode is of a conventional type such as an N+ to P− well diode. For example, diodes 21B and 22B formed adjacent to hot spot resistors 32, 33. The spacing between the hot spot resistors, sense diodes and heating resistors are a function of the photolithographic techniques used as well as the interconnection techniques used. The location of these diodes ensures that the maximum temperatures generated local to the hot spot resistors will be recorded. Sense diode 28 is fabricated in the die center to measure temperature there. Additional sense diodes such as diodes 21C, 24A and 24B are fabricated adjacent to the heating resistors but removed from hot spot resistors to ensure complete thermal coverage. Similarly, sense diodes and hot spot resistors configured in this same manner are fabricated in successive emulator ring configurations. Although more diodes and hot spot resistors can be fabricated per emulator ring configuration, only the minimum number necessary to thermally characterize to first order the portion of the die emcompassed by that ring configuration are fabricated in the best mode embodiment.

Figure 3:
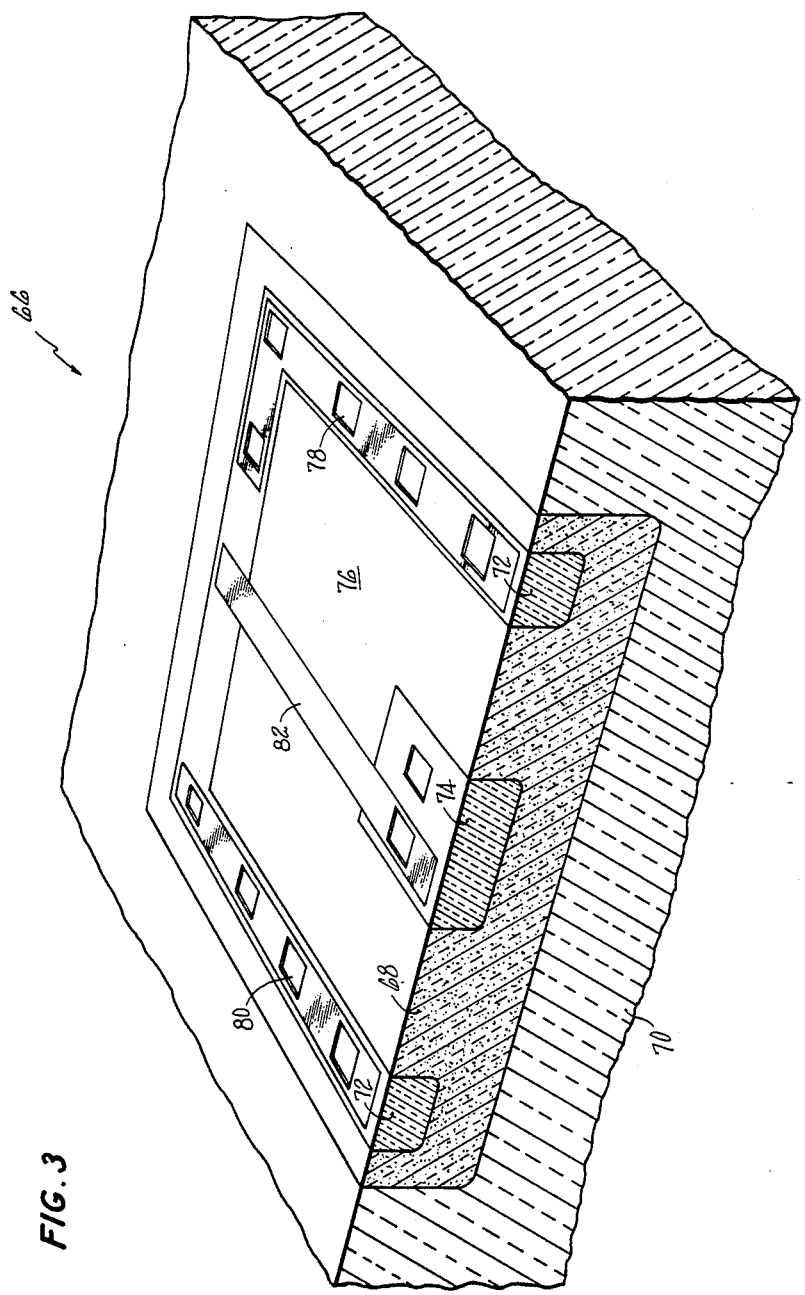
FIG. 3 is an illustration of a sense diode used in the programmable thermal emulator test die of FIG. 1.

FIG. 3 is an illustration partially in section and partially in perspective of a sense diode 66 used with the programmable thermal test die of Fig. 1. The sense diode is conventional in both materials and fabrication techniques. In the best mode embodiment an N+ to P− well CMOS diode is used. The starting semiconductor material is an N type silicon die. A conventional P− well diffusion is performed in area 68 of silicon substrate 70. Subsequently, a P+ dopant is introduced in region 72 for achieving ohmic contact to the P− well region. Conventional photolithographic techniques allow a region in the diode 74 to receive an N+ type diffusion. A protective oxide 76 is subsequently deposited onto the diode. Contact holes such as 78 and 80 are provided, and as is conventional, metallization 82 for electrical contact is finally deposited. Typically, the metal can be aluminum, although other metal such as chromium can be equivalently substituted. Those skilled in the art will note that although a typical N+ to P− well diode is specified for the best mode embodiment, other equivalent diodes such as a P+ to N− well on P type starting material may be substituted. In operation, the P well must be held to a lesser potential. In the best mode embodiment the substrate is raised to over +5 volts, the P well remains at ground potential and the N+ region is at a negative potential with respect thereto as is conventional.

Figure 4:
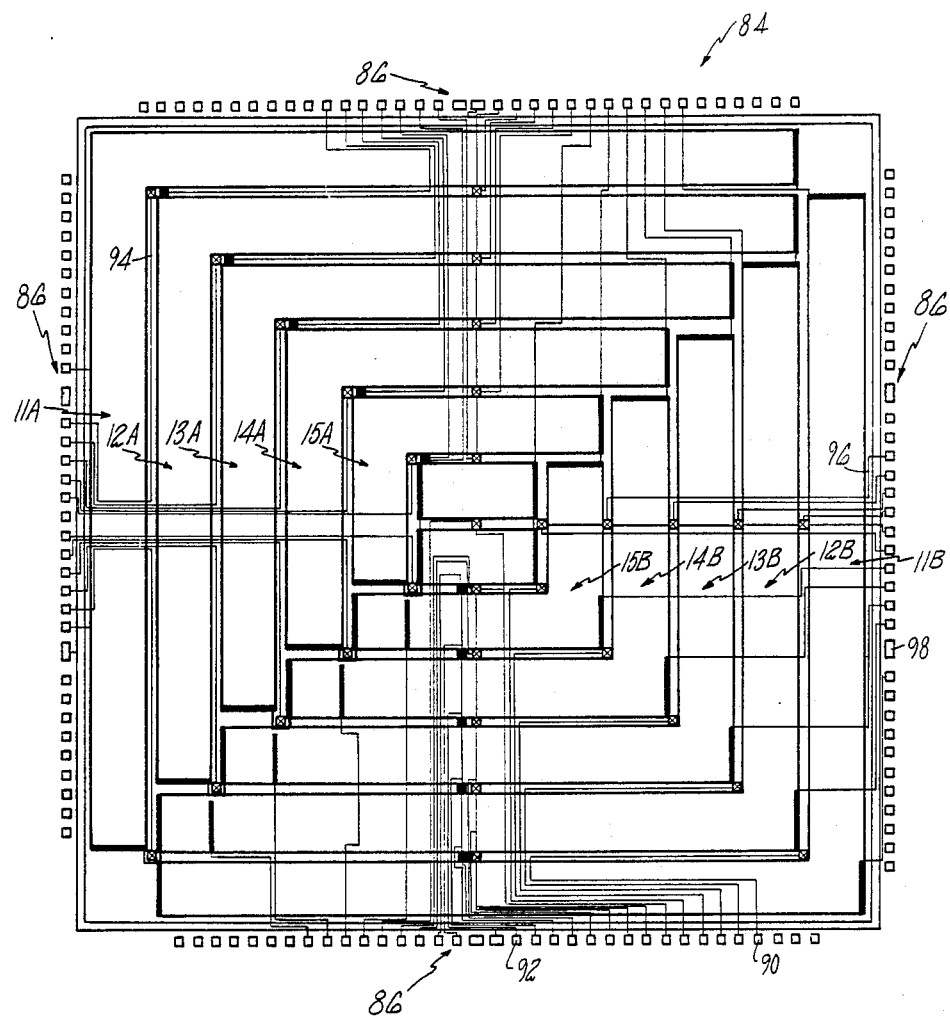
FIG. 4 is a planar illustration of a programmable thermal emulator test die provided according to the present invention fabricated for wire bonding, perimeter tape automated bonding, or perimeter "flip chip" interconnection.

FIG. 4 is an illustration of the programmable thermal emulator test die 10 of FIG. 1 fitted into a package 84 fabricated for conventional perimeter tape area bonding (TAB) or perimeter "flip chip" interconnection. With the bond pad array 86, of which pads 90 and 92 are a part.

Electrical connections between individual elements of the die and the bond pad array is accomplished through an interconnection array of leads, such as leads 94 and 96. The leads of the array are metal and are deposited by conventional photolithographic and metallization techniques. In the best mode embodiment the leads comprise aluminum deposited by evaporation and are isolated from the die by a layer of silicon dioxide or equivalent. Those skilled in the art will note that substrate bias pads, such as pad 98 are provided for use in establishing proper substrate polarity in biasing the sense diodes.

Unlike test dies of the prior art, the programmable thermal emulator test die provided according to the present invention allows for characterization of many types of interconnecting techniques and allows the engineer to compare perspective bonding technologies as well as optimize the product die for thermal behavior.

Similarly, although the invention has been shown and described with respect to a best mode embodiment thereof, it should be understood by those skilled in the art that various other changes, omissions, and additions thereto may be made therein without departing from the spirit and scope of the invention.

We claim:

1. A programmable die for simulating the thermal characteristics of a given product die, comprising:
    a die having a plurality of bond pads arrayed along the perimeter thereof;
    a plurality of heating resistor groups, each group including one or more linear resistive elements, said plurality of resistor groups being disposed in a lesser plurality of generally concentric rings on a major surface of said die;
    a plurality of sense diodes formed in said die surface at a plurality of locations in proximity to said heating resistor groups;
    a plurality of hot spot resistors formed in said die surface at another plurality of locations in proximity to said heating resistor groups and said sense diodes; and
    interconnection array, having a plurality of electrical signal conductors disposed on said die major surface, each connected between a related one of said bond pads and, alternately, to one of said heating resistor groups, said sense diodes, and said hot spot resistors, whereby said array conducts electrical signals applied to said bond pads to individual ones of said heating resistor groups, said sense diodes, and said hot spot resistors, whereby said heating resistors and said hot spot resistors provide, when excited, an actual surface temperature value for said die, and wherein said sense diodes each provide a signal indicative of said actual surface temperature.

2. The programmable die of claim 1, wherein said heating group resistors comprise a plurality of heating resistors disposed adjacent each other on said die surface to provide a substantially continuous heating surface along a respective one of said concentric rings, each said heating resistor in each said heating resistor group being connected through said interconnection array to individual ones of said bond pads, whereby said array further conducts electrical signals applied to said bond pads to individual ones of said plurality of heating resistors.

3. The programmable die of claim 2, wherein said plurality of sense diodes are each connected, alternately, to individual ones of said heating resistors, and to said hot spot resistors, for providing sense signals indicative of the magnitude of said electrical signals applied through said bond pads to the respective ones of said heating resistors and said hot spot resistors.

4. The programmable die of claim 2, wherein said heating resistors and said hot spot resistors comprise polycrystalline silicon.

5. The programmable die of claim 2, wherein said heating resistors and said hot spot resistors comprise diffused resistors.

6. The programmable die of claim 2, wherein said interconnection array is wire bonded to said bond pads.

7. The programmable die of claim 2, wherein said interconnection array is connected to said bond pads by tape automated bonding.

8. The programmable die of claim 2, wherein said interconnection array is connected to said bond pads by flip chip bonding.

9. The programmable die of claim 2, wherein the surface comprises N type silicon and wherein each of said sense diodes comprises a P well diffusion, a P+ N type diffusion, and metallization contacting selected portions of said N type diffusion.

* * * * *